United States Patent
Abraham et al.

(10) Patent No.: US 9,042,514 B2
(45) Date of Patent: May 26, 2015

(54) DOSE REDUCTION VIA DYNAMIC COLLIMATION ADJUSTMENT FOR TARGETED FIELD OF VIEW AND/OR DIGITAL TILT CT

(75) Inventors: Doug Abraham, Topsfield, MA (US); Lane Howitt, Reading, MA (US); Mitchell Surowiec, Beverly, MA (US); Carl DeVincent, Peabody, MA (US); David Rozas, Brighton, MA (US)

(73) Assignee: Analogic Corporation, Peabody, MA (US)

( * ) Notice: Subject to any disclaimer, the term of this patent is extended or adjusted under 35 U.S.C. 154(b) by 337 days.

(21) Appl. No.: 13/475,132

(22) Filed: May 18, 2012

(65) Prior Publication Data

US 2013/0308747 A1 Nov. 21, 2013

(51) Int. Cl.
 *A61B 6/03* (2006.01)
 *A61B 6/02* (2006.01)
 *A61B 6/06* (2006.01)
 *A61B 6/00* (2006.01)

(52) U.S. Cl.
 CPC ............ *A61B 6/03* (2013.01); *G01N 2223/419* (2013.01); *A61B 6/027* (2013.01); *A61B 6/032* (2013.01); *A61B 6/06* (2013.01); *A61B 6/4078* (2013.01); *A61B 6/4233* (2013.01); *A61B 6/4447* (2013.01)

(58) Field of Classification Search
 USPC ....................... 378/16, 147, 150, 151, 152, 17
 See application file for complete search history.

(56) References Cited

U.S. PATENT DOCUMENTS

| | | | |
|---|---|---|---|
| 6,229,869 B1 | 5/2001 | Hu | |
| 2010/0091937 A1* | 4/2010 | Raupach et al. | 378/16 |
| 2012/0128120 A1* | 5/2012 | De Man et al. | 378/16 |

* cited by examiner

*Primary Examiner* — Glen Kao
(74) *Attorney, Agent, or Firm* — Cooper Legal Group LLC (57) ABSTRACT

Among other things, one or more systems and/or techniques are described for dynamically adjusting, in a fan-angle direction, attenuation of radiation during an examination of an object such that portions of the object that are not represented in resulting (tilted/targeted) images of the object are exposed to less radiation than portions of the object that are represented in resulting (tilted/targeted) images of the object. As a rotating gantry is rotated, blades of a pre-object collimator are dynamically repositioned to selectively attenuate emitted radiation. A collimator adjustment component may be configured to determine how to reposition the blades based at least in part upon at least one of a desired tilt of the resulting (tilted) image(s), a translational position of the object, and a gantry rotation angle, for example.

20 Claims, 7 Drawing Sheets

DOSE REDUCTION VIA DYNAMIC COLLIMATION ADJUSTMENT FOR TARGETED FIELD OF VIEW AND/OR DIGITAL TILT CT

BACKGROUND

The present application relates to the field of imaging, and in particular computed tomography (CT) imaging where volumetric data of an object under examination is generated. It finds particular utility in medical applications, and in particular in medical applications where it is desirable to generate a tilted image(s) and/or to generate targeted images representative of a targeted field of view. However, it may also find utility in security and/or industrial applications, where images are developed based upon detected radiation (e.g., such as detected X-ray radiation and/or gamma radiation).

CT imaging modalities are useful to provide information, or images, of interior aspects of an object under examination. Generally, the object is exposed to radiation photons (e.g., such as X-rays, gamma rays, etc.), and an image(s) is formed based upon the radiation absorbed and/or attenuated by the interior aspects of the object, or rather an amount of photons that is able to pass through the object. Traditionally, the image (s) that is formed from the radiation exposure is a density image or attenuation image, meaning the image is colored/shaded as a function of the respective densities of sub-objects comprised within the object under examination. For example, highly dense sub-objects absorb and/or attenuate more radiation than less dense sub-objects, and thus a sub-object having a higher density, such as a bone or metal, for example, will be shaded differently than less dense sub-objects, such as muscle or clothing. However, more recently, multi-energy imaging systems (e.g., such as dual-energy CT scanners) have been utilized to discriminate sub-objects based upon more than density. Such systems are typically configured to distinguish sub-objects based upon density and other physical characteristics, such as atomic number, for example.

In a CT imaging modality, data generated from the detected radiation is generally reconstructed to form a plurality of image slices that, when combined, form a three-dimensional image of the object under examination. As will be further described below with respect to FIG. 3, image slices generated from detected radiation are typically perpendicular to a longitudinal axis of the object (e.g., the image slices are substantially parallel to one another and spaced in a z-direction parallel to an axis of rotation for the CT). However, in some diagnostic applications, it is desirable to generate image slices at a non-perpendicular orientation to better visualize certain structures within the object. For example, image slices at angles other than 90 degrees relative to the longitudinal axis of the object (e.g., non-transverse image slices) may be desirable when studying certain organs (e.g., the eyes).

Conventionally, a rotating gantry of the CT (e.g., to which the radiation source(s) and the detector array are attached) is mechanically tilted prior to the examination of an object to provide for such non-perpendicular orientations. That is, the rotating gantry may be tilted about a pivot point so that the rotating gantry may be positioned at different tilt angles (e.g., so that the axis of rotation of the gantry is inclined relative to the longitudinal axis of the object). More recently, in an effort to, among other things, reduce cost and complexity associated with the mechanical tilt design, techniques for reconstructing tilted images from volumetric data acquired from a non-tilted gantry (e.g., where the axis of rotation is substantially parallel to the longitudinal axis of object) have been proposed. In this way, the tilted images are created during image reconstruction as opposed to being created as a function of the tilt angle of the rotating gantry, for example.

While a digital tilt feature has numerous benefits over the mechanical tilt design, there are some drawbacks. For example, merely a fraction (e.g., 50%) of the portion of the object exposed to radiation may be represented in a digitally tilted image, and thus more radiation may be used than is necessary.

SUMMARY

Aspects of the present application address the above matters, and others. According to one aspect, a CT imaging modality is provided. The CT imaging modality comprises a radiation source configured to emit radiation and a detector array configured to detect radiation. The CT imaging modality also comprises a pre-object collimator configured to dynamically adjust, in a fan-angle direction, attenuation of emitted radiation during an examination of an object.

According to another aspect, a method for imaging an object is provided. The method comprises dynamically adjusting attenuation of a fan beam via a pre-object collimator during an examination of an object from which one or more images of the object are generated.

According to yet another aspect, a computer readable medium is provided where the computer readable medium comprises computer executable instructions that when executed via a processor perform a method. The method comprises rotating a gantry comprising a radiation source and a detector array about an object during an examination of the object. The method also comprises dynamically adjusting via a pre-object collimator, in a fan-angle direction, attenuation of radiation emitted by the radiation source while rotating the gantry to vary an amount of radiation to which the object is exposed as a function of a rotation angle of the gantry relative to the object.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques are described for varying attenuation of radiation in a fan-angle direction during an examination of an object. For example, a pre-object (e.g., pre-patient) collimator may be comprised of one or more blades (e.g., leafs) configured to be dynamically repositioned during an examination of the object. The blade(s) is configured to attenuate at least a portion of the radiation in the fan-angle direction. In this way, by dynamically repositioning the blade(s) during the examination of the object (e.g., as a rotating gantry is being rotated about the object), the attenuation of radiation in a fan-angle direction may be varied, for example. By way of example, in one embodiment, the blade(s) is configured to attenuate nearly 100% of the radiation that impinges the blade(s). As such, by dynamically repositioning the blade(s) during an examination, the size of the fan-beam changes during the examination. In another embodiment, the blade(s) is configured to attenuate less than 100% of the radiation that impinges the blade(s). Therefore, the size of the fan-beam may remain substantially constant, for example, but the portion of the fan-beam that is at least partially attenuated by the blade(s) may be varied. By way of example, at a first rotating gantry angle, 20% of the fan-beam may be at least partially attenuated by the blade(s) and at a second rotating gantry angle, 50% of the fan-beam may be at least partially attenuated by the blade(s).

Such techniques and/or systems may find particular applicability in the context of medical CT scanners configured to generate digitally tilted images and/or targeted images. That is, stated differently, a pre-object collimator may be configured to vary the attenuation of radiation in the fan-angle direction such that detector cells (or information derived from the detector cells) that are not utilized in reconstructing a digitally tilted image and/or targeted image are not exposed to radiation (or are exposed to less radiation). In this way, the dose applied to an object, such as a patient, may be less when compared to conventional medical CT scanners configured to generate digitally tilted images and/or targeted images.

Figure 1:
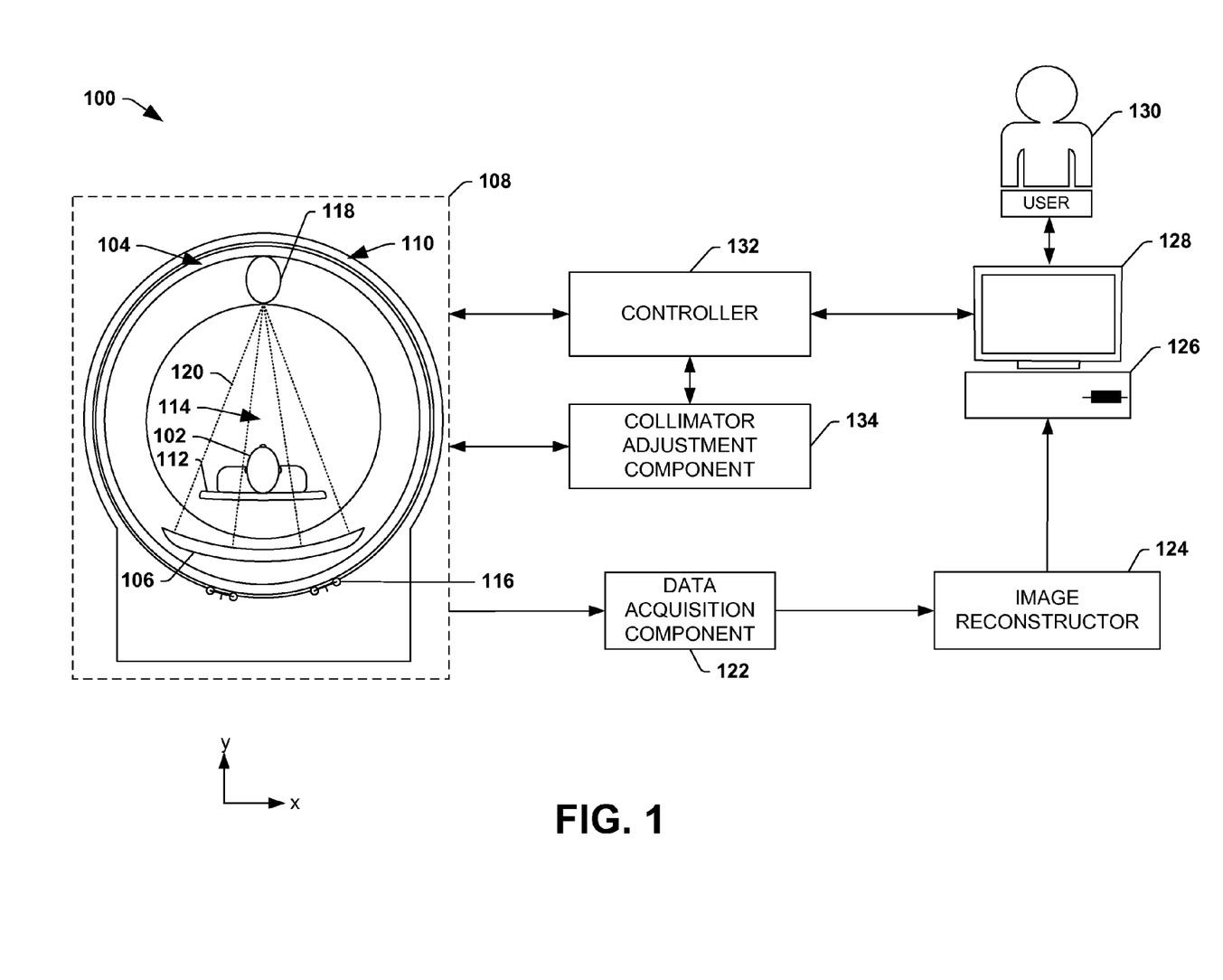
FIG. 1 is a schematic block diagram illustrating an example examination environment for examining an object.

FIG. 1 illustrates an example environment 100 wherein one or more of the techniques and/or systems described herein may find applicability. More particularly, FIG. 1 illustrates an example computed tomography (CT) scanner configured to examine an object(s) 102 (e.g., a patient, suitcase, etc.) and generate one or more images therefrom. It may be appreciated that while specific reference is made herein to CT imaging modalities, the instant application may find applicability to other radiation imaging modalities (e.g., such as digital/projection radiology, SPECT, mammography, etc.) where varying the attenuation of radiation in the fan-angle direction may be useful.

In the example environment 100, an examination unit 108 of the imaging modality is configured to examine one or more objects 102. The examination unit 108 can comprise a rotating gantry 104 and a (stationary) support structure 110 (e.g., which may encase and/or surround as least a portion of the rotating gantry 104 (e.g., as illustrated with an outer, stationary ring, surrounding an outside edge of an inner, rotating ring)). During an examination of the object(s) 102, the object (s) 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about the object(s) 102 by a rotator 116, such as a motor, drive shaft, chain, roller truck, etc.

The rotating gantry 104 may surround a portion of the examination region 114 and may comprise a radiation source 118 (e.g., an ionizing x-ray source, gamma radiation source, etc.) and a detector array 106 that is mounted on a substantially diametrically opposite side of the rotating gantry 104 relative to the radiation source(s) 118. During an examination of the object(s) 102, the radiation source(s) 118 emits fan, cone, wedge, and/or other shaped radiation 120 configurations from a focal spot(s) of the radiation source 118 (e.g., a region within the radiation source 118 from which radiation 120 emanates).

The example environment 100 further comprises a pre-object collimator (not shown) and a collimator adjustment component 134. As will be described in more detail below, the pre-object collimator, which may be positioned between the radiation source 118 and the examination region 114 (and more particularly the object), is configured to attenuate, in the fan-angle direction (e.g., which varies in an x,y plane as the rotating gantry 104 rotates about the object(s) 102), at least a portion of the emitted radiation 120. More particularly, as the rotating gantry rotates, one or more radiation attenuating blades of the pre-object collimator, for example, may be dynamically repositioned to reduce radiation exposure to aspects of the object(s) 102 that are not intended to be represented in a (digitally tilted/targeted) image resulting from the examination.

The collimator adjustment component 134, which may be located on the stationary side of the imaging modality or on the rotating gantry 104, may be configured to provide information to the pre-object collimator regarding how the one or more radiation attenuating blades should be repositioned as a function of, among other things, a z-position of the object support 112 (e.g., into and out of the page), a desired tilt angle of the image(s) resulting from the examination, a gantry rotation angle, and/or a trajectory of radiation 120 relative to the object(s) 102. Thus, the collimator adjustment component 134 may be configured to receive information about the position of the object(s) 102 and/or the rotating gantry 104 and to determine what aspects of the object(s) 102 are to be exposed to radiation 120.

Emitted radiation 120 that traverses the object(s) 102 may be attenuated differently by different aspects of the object(s) 102. Because different aspects attenuate different percentages of the radiation 120, an image(s) may be generated based upon the attenuation, or variations in the number of photons that are detected by cells of the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to a data acquisition component 122 configured to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that was emitted while the radiation source 118 was at a particular angular range relative to the object(s) 102. Based upon the compiled signals, the data acquisition component 122 can generate projection data indicative of the compiled signals, for example.

The example environment 100 also illustrates an image reconstructor 124 that is operably coupled to the data acquisition component 122 and is configured to generate one or more images representative of the object(s) 102 under examination based at least in part upon signals output from the data acquisition component 122 using suitable analytical, iterative, and/or other reconstruction technique (e.g., tomosynthesis reconstruction, back-projection, iterative reconstruction, etc.). For example, in a CT imaging application, the image reconstructor 124 may be configured to generate one or more image slices of the object(s) 102, respectively representative of a portion, or slice, of the object(s) 102. Such image slices may be combined, for example, to generate one or more images for presentation to a user 130, for example.

The example environment 100 also includes a terminal 126, or workstation (e.g., a computer), configured to receive image(s) from the image reconstructor 124, which can be displayed on a monitor 128 to a user 130 (e.g., security personnel, medical personnel, etc.). In this way, the user 130 can inspect the image(s) to identify areas of interest within the object(s) 102. The terminal 126 can also be configured to receive user input which can direct operations of the object examination apparatus 108 (e.g., a speed of gantry rotation, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed. The controller 132 may also be configured to receive information from the examination unit 108, such as, for example, information related to a gantry rotation angle.

It may be appreciated that the components of the illustrated CT imaging modality and/or the features described with respect to respective components are intended to provide an example configuration and are not intended to be construed as limiting the scope of the instant application, including the claims. That is, an imaging modality may comprise additional components and/or different components than those described above and/or one or more of the described components may be configured to perform additional and/or different actions. Moreover, the arrangement of components may be different than the illustrated arrangement. For example, in one embodiment, the data acquisition component 122 may be coupled to the detector array 106 and mounted to the rotating gantry 104.

Figure 2:
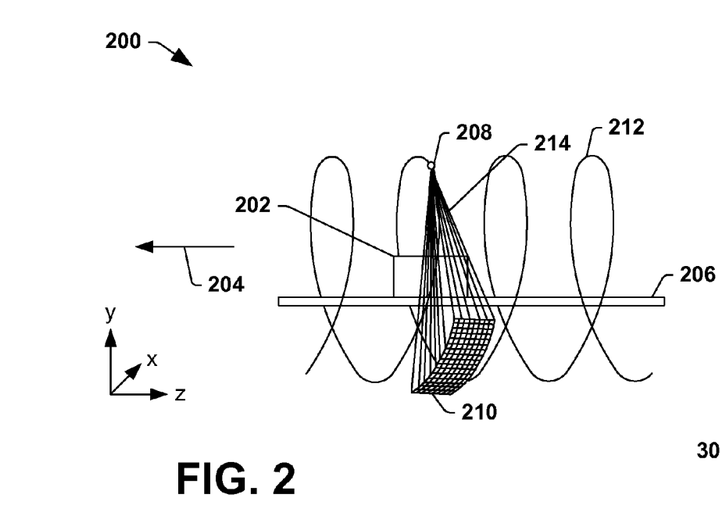
FIG. 2 illustrates a functional diagram of a helical CT imaging modality.

FIG. 2 is a functional diagram 200 of a helical scan performed via a CT imaging modality, such as in medical and/or security applications. In such an imaging modality, an object 202 (e.g., 102 in FIG. 1) under examination is translated 204 (e.g., at either constant speed or in a step-and shoot manner) in a direction parallel to a longitudinal axis of the object 202 (e.g., along a z-axis), via an object support 206 (e.g., 112 in FIG. 1). The object 202 is exposed to radiation 214 while the object 202 is being translated and/or between translations. That is, one or more radiation sources 208 (e.g., 118 in FIG. 1) are configured to emit radiation 214, causing the object 202 to be exposed to radiation 214. A detector array 210 (e.g., 106 in FIG. 1), mounted on a substantially diametrically opposite side of the object 202 relative to the radiation source(s) 208, is configured to detect radiation 214 that has traversed the object 202. In this way, by emitting and detecting radiation 214, the object 202 is examined.

Figure 3:
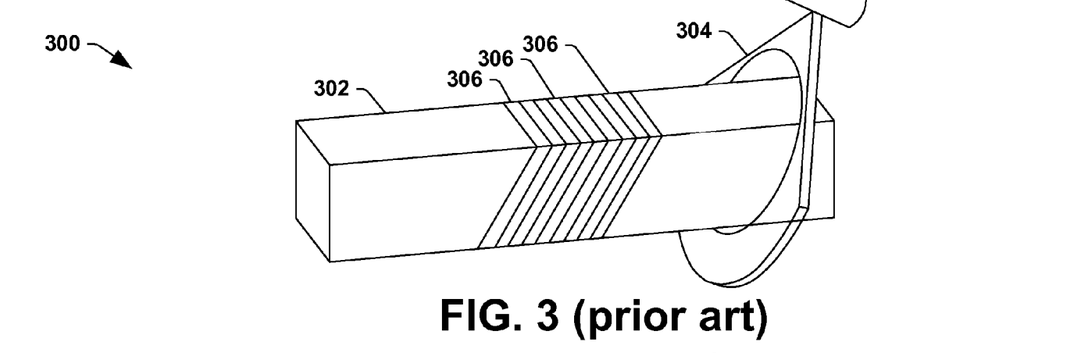
FIG. 3 illustrates object slices represented in tilted image slices obtained from an object being examined via a mechanically tilted rotating gantry.
Figure 4:
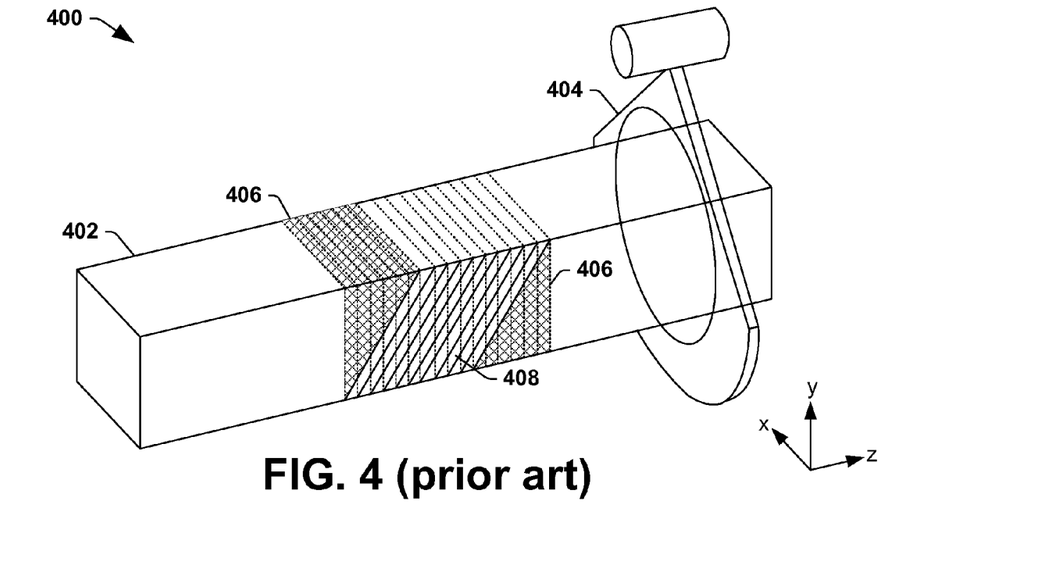
FIG. 4 illustrates object slices represented in tilted image slices obtained via a digital tilt technique.

In a CT imaging modality, the radiation source(s) 208 and the detector array 210 are typically rotated about the object 202 (e.g., in an x,y plane) via a rotating gantry (e.g., 104 in FIG. 1) during the examination. Thus, in an environment where the object 202 is translated at a substantially constant speed, such a rotation may cause the radiation source(s) 208 and/or the detector array 210 to follow a spiral or helical-like trajectory 212 relative to the object (e.g., where the radiation source(s) 208 and detector array 210 do not move in the z-direction, and thus the helical trajectory is established by the combination of the x/y rotation of the source 208 and detector array 210 and the z-direction translation 204 of the object 202). As the object 202 is translated, data for a prescribed number of slices of the object 202 may be acquired via detected radiation 214.

Where the radiation source(s) 208 and the detector array 210 are configured to rotate about the object 202, an axis of rotation may be defined as a center point of the rotation (e.g., an axis about which the rotating gantry and/or the source 208 and/or detector array 210 rotates). In an environment where the rotating gantry is not tilted (e.g., as illustrated in FIGS. 2 and 4), the axis of rotation is typically parallel to the longitudinal axis of the object 202 and/or parallel to the direction of translation 204. In an environment where the rotating gantry is tilted (e.g., as illustrated in FIG. 3), the axis of rotation may be inclined (e.g., oriented at an angle other than zero degrees) relative to the longitudinal axis of the object 202 and/or inclined relative to the direction of translation 204.

It may be appreciated that radiation 214 may be emitted from the radiation source 208 in a multitude of directions. In one example, emitted radiation 214 may form a cone shape (e.g., in x,y and z directions) as it emanates from the radiation source 208 to the detector array 210, which may at times be referred to a cone beam. In another example, emitted radiation 214 may form a fan shape (e.g., in x,y directions) as it emanates from the radiation source 208 to the detector array 210, which may at times be referred to as a fan beam. It may be appreciated that a cone beam may be said to comprise one or more fan beams. For example, where a fan beam is comprised within an x,y plane, a cone beam may comprise multiple fan beams that are 'stacked' on top of one another or adjacent to one another in the z direction. Adjacent fan beams (that represent slices through the conical shaped cone beam) may vary in width, where a centermost fan beam (slicing through the greatest diameter of the cone beam) may have a greatest width and outmost fan beams may have a smallest width. For purposes of the instant application, the trajectory of emitted radiation may be described in terms of at least two directional components: a fan-angle direction and a cone-angle direction.

It may be appreciated that even though a cone shape or cone beam has a 3D connotation (x,y and z components), the cone-angle direction is merely a 2D construct (because it pertains to a direction, not a volume). The cone-angle direction typically refers to a direction substantially parallel to the axis of rotation for the rotating gantry. For example, where the rotating gantry is not tilted, the cone-angle direction may be substantially parallel to a longitudinal axis of the object 202 under examination and/or parallel to a direction of translation 204 of the object 202 (e.g., parallel to the z-axis). Where the rotating gantry is tilted, however, the cone-angle direction may be inclined relative to the longitudinal axis of the object 202 under examination or the direction of translation 204 of the object 202.

The fan-angle direction pertains to a direction of a fan-angle, where a size or width of a fan beam corresponds to the angle (fan angle) of a fan beam (e.g., a larger fan-angle corresponds to a wider fan beam and a smaller fan-angle corresponds to a narrower fan beam). Thus, in the illustrated example, the where the radiation source 208 is directly above the object 202, the fan-angle direction can be said to be in the x direction as the beam 'fans out' at an angle in the x-direction to impinge upon the detector array 210 that is directly below the object 202 (where the detector array 210 substantially extends in the x-direction). As the rotating gantry is rotated (e.g., within an x,y plane) such that the radiation source 208 is to one side of the object 202 and the detector array 210 is to the other side of the object, the fan-angle direction can be said to be in the y-direction as the beam 'fans out' at an angle in the y-direction to impinge upon the detector array 210 that now substantially extends in the y-direction (after a 90 degree rotation of the gantry). It may be appreciated that the fan-angle direction thus lies within a plane (e.g., the x,y plane) that is substantially perpendicular to the axis of rotation.

Also for purposes of the instant application, a gantry rotation angle is typically defined as a number of degrees that the rotating gantry has rotated away from a predefined zero-degree reference. For example, zero-degrees may be defined as a position of the rotating gantry that causes the radiation source 208 to be positioned directly above the object 202. Thus, when the rotating gantry rotates (e.g., within the x,y plane) such that the radiation source 208 becomes positioned directly below the object 202 (and the detector array is directly above or over the object), the gantry rotation angle may be approximately 180-degrees.

FIG. 3 illustrates an example environment 300 of a conventional tilted CT scanner, where a rotating gantry (e.g., 104 in FIG. 1) is mechanically tilted relative to the longitudinal axis of the object 302 (e.g., parallel to the z-axis). More particularly, FIG. 3 illustrates a tilted field of view 304, which is caused by mechanically tilting the rotating gantry (e.g., including the radiation source 308 and the detector array) to a desired angle (e.g., equal to the desired tilt of the images). By way of example, prior to an object undergoing a diagnostic examination, a field of view 304 may be tilted by mechanically tilting, among other things, the radiation source 308, rotating gantry, and detector array. In this way, an axis of rotation and a cone-angle direction may be inclined relative to the longitudinal axis of the object 302 and the field of view 304 may be titled with respect to the object 302. Image slices, respectively representative of a slice 306 of the object, are typically parallel to the field of view 304. As such, when the field of view 304 is tilted with respect to the object 302, the image slices are also tilted relative to the object 302, as shown by the tilted slices 306 of the object.

FIG. 4 illustrates an example environment 400 of a conventional CT scanner configured to digitally tilt one or images slices respectively depicting a slice of the object 402 while not tilting a field of view 404 (e.g., 304 in FIG. 3). More particularly, during the examination of the object 402, the image data is acquired with the field of view 404 being substantially perpendicular to the longitudinal axis of the object 402 (e.g., which is parallel to the z-axis). As such, image slices derived from data produced during the examination would typically respectively depict a slice 406 of the object 402 that is substantially parallel to the field of view 404 (e.g., where boundaries of respective slices are illustrated by dashed lines). Thus, the image slices would not be tilted as provided for using the mechanical tilt feature of FIG. 3. As such, digitally tilted image slices 408 may be created by interpolating non-tilted image slices that represent a range of the object 402 being represented in the digitally tilted image slices (e.g., where boundaries of respective tilted slices are illustrated by solid diagonal lines passing through the object 402). It may be appreciated that the degree of tilt relative to the longitudinal axis of the object 402 may be a function of user preference, for example.

Because the non-tilted images represent a range of the object 402 being represented in the digitally titled image slices, at least some portions of the object 402 exposed to radiation (e.g., and represented in the non-tilted image slices) may not be represented in the digitally tilted image slices 408. For example, the checkered or cross-hatched portions of object 402 may be exposed to radiation, but information regarding these portions may not be included in the digitally tilted image slices 408. As such, a portion of the object (e.g., the checkered or cross-hatched portions) may be exposed to radiation unnecessarily, for example.

Figure 5:
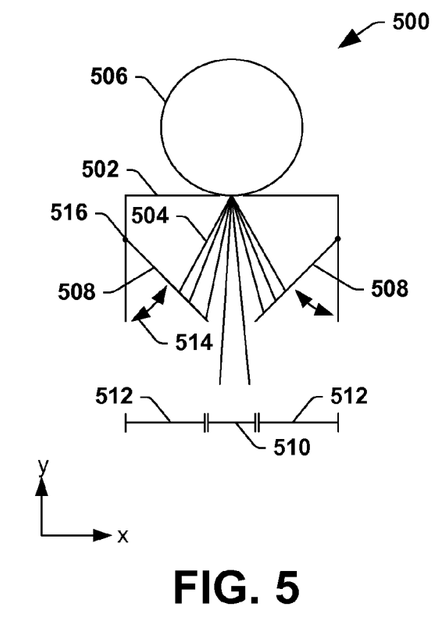
FIG. 5 illustrates an example pre-object collimator.
Figure 6:
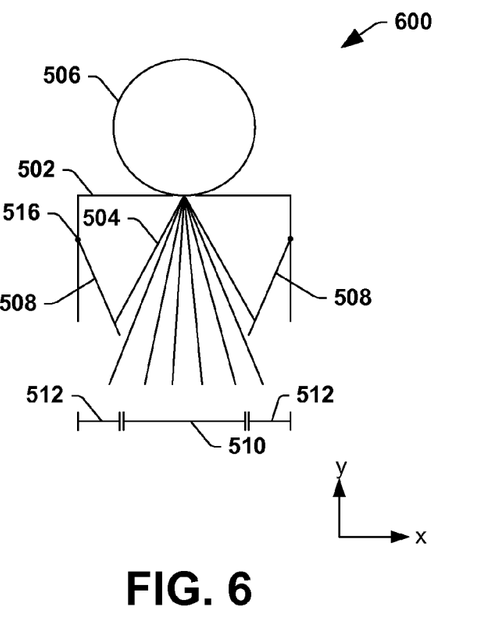
FIG. 6 illustrates an example pre-object collimator.

FIGS. 5-6 illustrate example environments 500, 600 of an imaging modality comprising a pre-object collimator 502 (e.g., such as a multi-leaf collimator) configured to dynamically adjust, in a fan-angle direction, attenuation of emitted radiation 504 during an examination of an object (e.g., 102 in FIG. 1). That is, stated differently, the pre-object collimator 502 may be positioned between a radiation source 506 (e.g., 208 in FIG. 2) and an object under examination (e.g., 202 in FIG. 2) and may be configured to, at times, attenuate a portion of the emitted radiation 504 to reduce a desired amount of radiation exposure to the object, where the attenuation occurs in a fan-angle direction. In the illustrated example, a fan beam 'fans out' in the x-direction, and thus the pre-object collimator closes or 'clamps-down' to greater (FIG. 5) or lesser (FIG. 6) degrees in the x-direction such that the width of the fan beam (upon exiting the pre-object collimator 502) may be adjusted in the x-direction (e.g., attenuation of emitted radiation is adjusted in the fan-angle direction (e.g., the x-direction in the illustrated example)). In this way, the pre-object collimator 502 may be configured to expose little to no radiation to the checkered or cross-hatched portions of the object 402 illustrated in FIG. 4 when information regarding these portions is not included in (tilted) image slices and/or targeted images produced from or derived from the examination, for example.

It may be appreciated that as used herein, a pre-object collimator may be a separate mechanical component positioned between the radiation source 506 and an object and/or it may be part of the radiation source 506. By way of example, a shutter of the radiation source 506 may serve as a pre-object collimator, for example. As illustrated, the pre-object collimator 502 may be comprised of one or more blades 508 (e.g., also referred to as leaves) extending in the fan-angle direction and respectively configured to attenuate a portion of the radiation 504 traversing the pre-object collimator 502. That is, stated differently, the blades 508 may be at least partially comprised of a radiation attenuating material, such as lead or tungsten, making the blades 508 at least partially opaque to radiation. For example, in FIGS. 5-6, radiation 504 impinging the blades 508 is unable to traverse the blades 508 while radiation that does not impinge the blades 508 may be able to traverse the pre-object collimator 502 and impinge an object under examination, for example. In this way, the pre-object collimator 502 may be said to be comprised of one or more regions of substantially no attention 510 and one or more regions of attenuation 512 (e.g., where the region(s) of attenuation 512 may be defined as a region comprising one or more radiation attenuating blades 508).

One or more of the blades 508 may be dynamically repositioned 514 by the pre-object collimator 502 during a rotation of the radiation source 506 and/or detector array to cause the attenuation of emitted radiation (e.g., emitted in a fan-angle direction) to be dynamically adjusted. For example, as illustrated in FIG. 6, the blades 508 may be furthered opened to create a larger opening, in the fan-direction, relative to the opening in FIG. 5. Stated differently, the region of substantially no attenuation 510 may be dynamically adjusted by the pre-object collimator 502. For example, FIG. 6 illustrates the region of substantially no attenuation 510 increased in size relative to its size in FIG. 5 and the regions of attenuation 512 decreased in size relative to their respective sizes in FIG. 5. It may also be appreciated that by dynamically repositioning one or more blades 508 (e.g., and/or adjusting the size of the region of substantially no attenuation 510), a fan-beam of radiation 504 may increase or decrease in size with the repositioning of the blades 508, if the blades 508 are configured to attenuate substantially 100% of the radiation impinging thereon as illustrated in FIGS. 5-6.

It may be appreciated that numerous techniques are contemplated for dynamically repositioning the blades 508. For example, in the illustrated embodiment, the blades 508 are coupled to the pre-object collimator 502 via mechanically driven hinges 516 configured to maneuver the blades as specified (e.g., by a collimator adjustment component) based upon, among other things, a trajectory of emitted radiation, a desired effective digital tilt of reconstructed image slices, and/or a gantry rotation angle, for example. However, other apparatus for driving or maneuvering/repositioning the blades 508 of the pre-object collimator 502 are also contemplated. For example, in another embodiment, the blades 508 may be attached to a hydraulic or air-driven piston configured to reposition the blades 508 as specified by the collimator adjustment component, for example.

Figure 7:
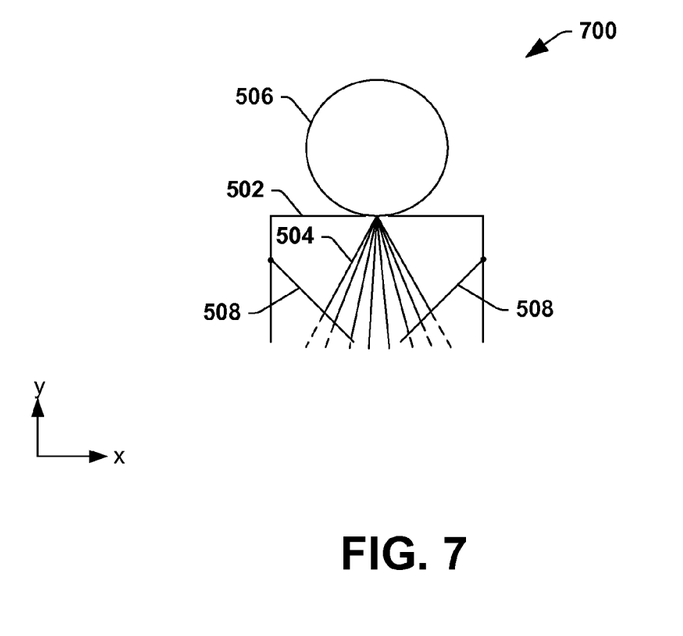
FIG. 7 illustrates an example pre-object collimator.

FIGS. 5-6 illustrate the blades 508 as being configured to attenuate substantially all of the radiation 504 (e.g., emitted in a fan-angle direction) impinging thereon. However, in another embodiment, the blades 508 may be configured to attenuate less than all of the radiation that impinges the blades 508. For example, FIG. 7 illustrates an example environment 700 where one or more blades 508 may be configured to allow some, but not all, of the radiation 504 impinging thereon to traverse the blades 508 (e.g., as illustrated by the lines changing from solid to dashed upon passing the blades 508) and to enter an examination region. In this way, a width of the fan beam (upon exiting the pre-object collimator 502) may remain substantially constant, but where outer portions of the beam are less "intense". Images may thus be acquired from cells of the detector array not used to reconstruct the tilted images (e.g., to assist in image reconstruction of an image slice and reduce artifacts) while reducing dosage to an object, for example. As an example, the blades may attenuate enough of the radiation to provide for a recovery of an attenuation value during reconstruction within a 10% error relative to what would be the correct value for detector cells not used to reconstruct the tilted images. In yet another embodiment (not shown), one or more of the blades 508 may be tapered, stepped, etc. such that a first portion of the blades (e.g., a thick portion) attenuates substantially all of the radiation impinging thereon and a second portion of the blades (e.g., a thinner portion) attenuates less than all of the radiation impinging thereon (e.g., thus allowing at least some radiation to traverse the thinner portion of the blades 508).

As previously described, the positioning and/or repositioning of blades may be a function of, among other things, the desired angle of the digitally tilted image slices (or a desired orientation of a targeted object), a z-position of an object support (e.g., assuming the rotating gantry rotates in an x,y plane), and the gantry rotation angle and/or a trajectory of emitted radiation. In this way, the field of view is targeted/directed to expose a portion of the object represented in the image to more radiation than a portion of the object not represented in the image.

Figure 8A:
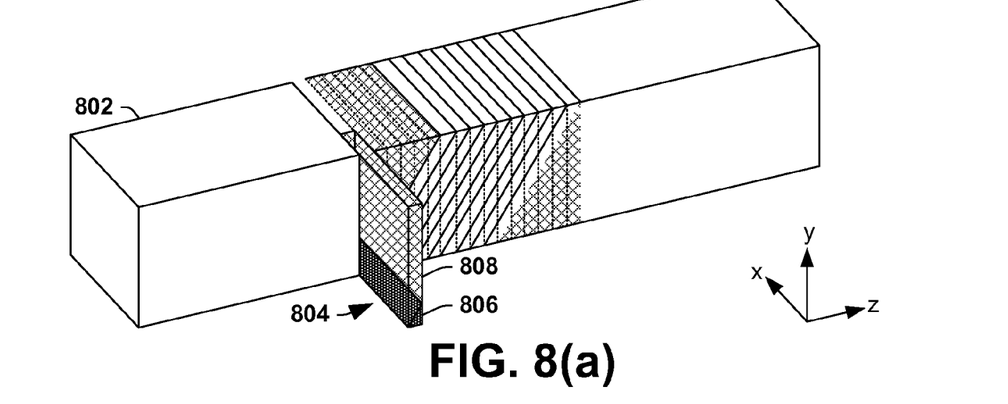
FIG. 8(a) represents an object slice that may be represented in a digitally tilted image.
Figure 8B:
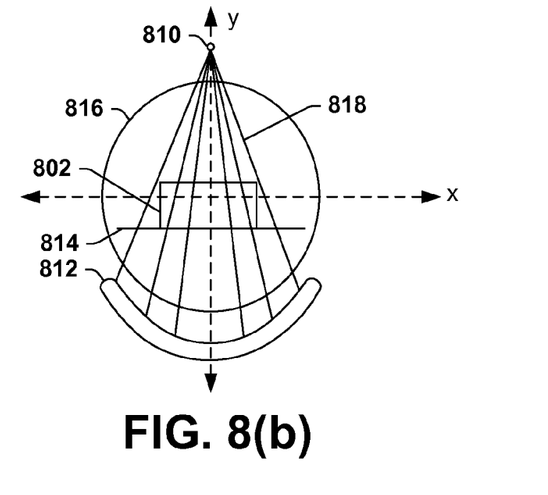
FIG. 8(b) represents a fan beam emitted when a rotating gantry is at a first gantry rotation angle.
Figure 8C:
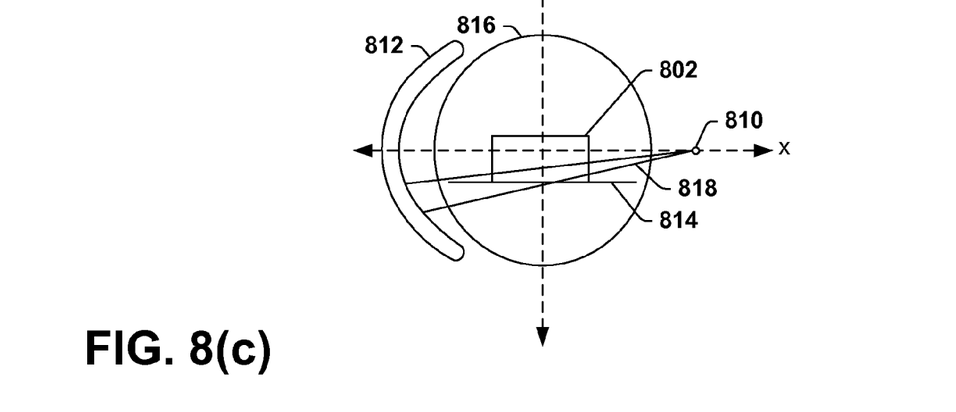
FIG. 8(c) represents a fan beam emitted when a rotating gantry is at a second gantry rotation angle.

FIGS. 8(*a*)-(*c*) illustrate how a pre-object collimator (e.g., 502 in FIGS. 5-7) may be configured to dynamically adjust the attenuation of radiation in a fan-angle direction as an object 802 (e.g., 402 in FIG. 4) is being examined. For example, suppose that the rotating gantry, radiation source, and detector array are positioned to examine an object slice 804 of the object 802 (e.g., as may be determined based upon the z-position of an object support on which the object 802 is resting). As a function of calculations performed by a collimator adjustment component, for example, it may be determined that merely a bottom portion 806 of the object slice 804 is represented in a digitally tilted image(s) and/or in targeted images (e.g., where the bottom portion is represented by a darkened pattern). As such, the collimator adjustment component may provide information to the pre-object collimator, which the pre-object collimator may utilize to dynamically adjust attenuation of radiation in the fan-angle direction (e.g., to change the field of view such that it targets a portion of the object slice 804). In this way, a portion 808 of the object slice 804 that is not represented in the digitally tilted image and/or targeted image (e.g., as represented by the checkerboard/cross-hatch pattern) may be exposed to less radiation than the bottom portion 806 of the object slice 804. Thus, the total dose applied to the object 802 may be less, for example, than a traditional digital tilt apparatus where all of the object slice 804 (e.g., including portions 806 and 808) is typically exposed to a substantially uniform amount of radiation.

FIGS. 8(*b*)-(*c*) illustrate a radiation source 810 (e.g., 208 in FIG. 2) and a detector array 812 (e.g., 210 in FIG. 2) at various rotational angles relative to the object 802 (e.g., positioned on an object support 814 (e.g., 206 in FIG. 2) in an examination region 816 (e.g., 114 in FIG. 1)). It may be appreciated that in such examples, the fan-angle direction may be parallel to a plane of the page and a cone-angle direction may be into and out of the page (e.g., with the object 802 being translated in the cone-angle direction).

As illustrated in FIG. 8(*b*), when the radiation source 810 is positioned above the object 802, the pre-object collimator may attenuate little to no radiation 818 (e.g., 504 in FIGS. 5-7) in the fan-angle direction because substantially all of the radiation traversing the object traverses the bottom portion 806 of the object slice 804, which is represented in the digitally tilted image. However, as the rotating gantry is rotated, causing the trajectory of radiation 818 to change relative to the object 802, the pre-object collimator may be configured to dynamically adjust, in a fan-angle direction, attenuation of emitted radiation 818. For example, as illustrated in FIG. 8(*c*), when the radiation source 810 is positioned to the right side of the object 802 (e.g., such that the fan-angle direction is in the y-direction), the pre-object collimator may attenuate radiation that would traverse an upper half of the object slice 804 because the upper half of the object slice 804 is not represented in the digitally tilted image. That is, stated differently, the pre-object collimator may attenuate radiation that would impinge portion 808 of the object slice 804 (e.g., that is not represented in the digitally tilted image), but may allow radiation that would at least partially impinge portion 806 of the object slice 804 (e.g., that is represented in the digitally tilted image) to pass through the pre-object collimator substantially unattenuated, for example.

Figure 9A:
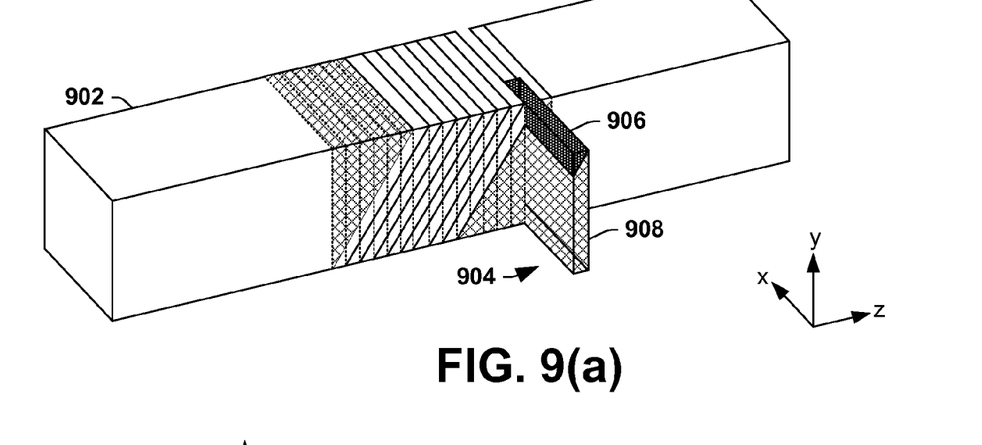
FIG. 9(a) represents an object slice that may be represented in a digitally tilted image.
Figure 9B:
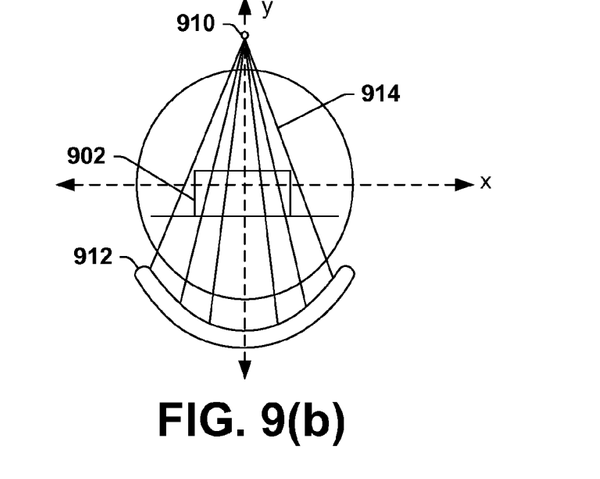
FIG. 9(b) represents a fan beam emitted when a rotating gantry is at a first gantry rotation angle.
Figure 9C:
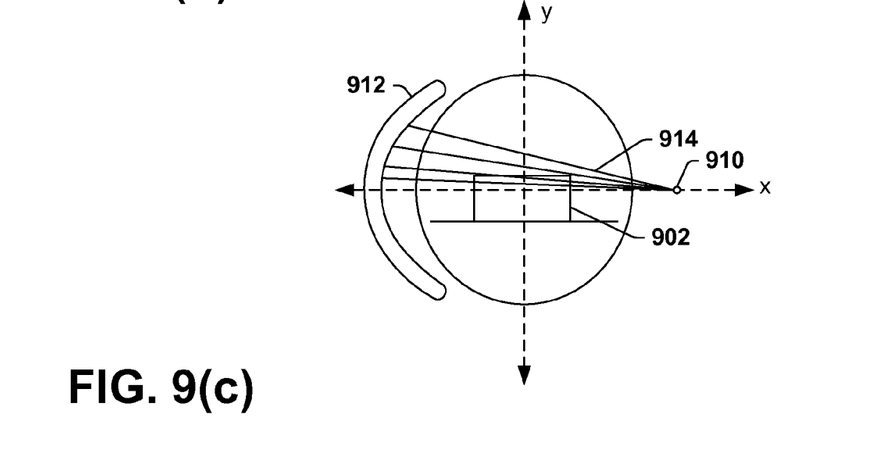
FIG. 9(c) represents a fan beam emitted when a rotating gantry is at a second gantry rotation angle.

FIGS. 9(*a*)-(*c*) illustrate yet another example of how a pre-object collimator (e.g., 502 in FIGS. 5-7) may be configured to dynamically adjust the attenuation of radiation when a second object slice 904 of an object 902 (e.g., 802 in FIG. 8) is examined to generate a corresponding image slice. For example, as a function of calculations performed by a collimator adjustment component, it may be determined that merely a top portion 906 of the second object slice 904 is represented in a digitally tilted image(s) and/or in a targeted image (e.g., where the top portion is represented by a darkened pattern). As such, the collimator adjustment component may provide information to the pre-object collimator, which the pre-object collimator may utilize to dynamically adjust attenuation of radiation in the fan-angle direction. In this way, a portion 908 of the second object slice 904 that is not represented in the digitally tilted image and/or the targeted image (e.g., as represented by the checkerboard/cross-hatch pattern) may be exposed to less radiation than the top portion 906 of the second object slice 904.

FIGS. 9(*b*)-(*c*) illustrate a radiation source 910 (e.g., 810 in FIG. 8) and a detector array 912 (e.g., 812 in FIG. 8) at various rotational angles relative to the object 902. It may be appreciated that in such examples, the fan-angle direction may be parallel to a plane of the page and a cone-angle direction may be into and out of the page (e.g., with the object 902 being translated in the cone-angle direction).

As illustrated in FIG. 9(*b*), when the radiation source 910 is positioned above the object 902, the pre-object collimator may attenuate little to no radiation 914 (e.g., 504 in FIGS. 5-7) in the fan-angle direction because substantially all of the radiation traversing the object traverses the top portion 906 of the second object slice 904, which is represented in the digitally tilted image. However, as the rotating gantry is rotated, causing the trajectory of radiation 914 to change relative to the object, the pre-object collimator may be configured to dynamically adjust, in a fan-angle direction, attenuation of emitted radiation 914. For example, as illustrated in FIG. 9(*c*), when the radiation source 910 is positioned to the right side of the object 902 (e.g., such that the fan-angle direction is in the y-direction), the pre-object collimator may attenuate radiation that would traverse a bottom half of the second object slice 904 because the bottom half of the second object slice 904 is not represented in the digitally tilted image. The pre-object collimator may not, however, attenuate radiation 914 at least partially traversing the upper portion 906 because the upper portion 906 may be represented in the digitally tilted image, for example.

Figure 10:
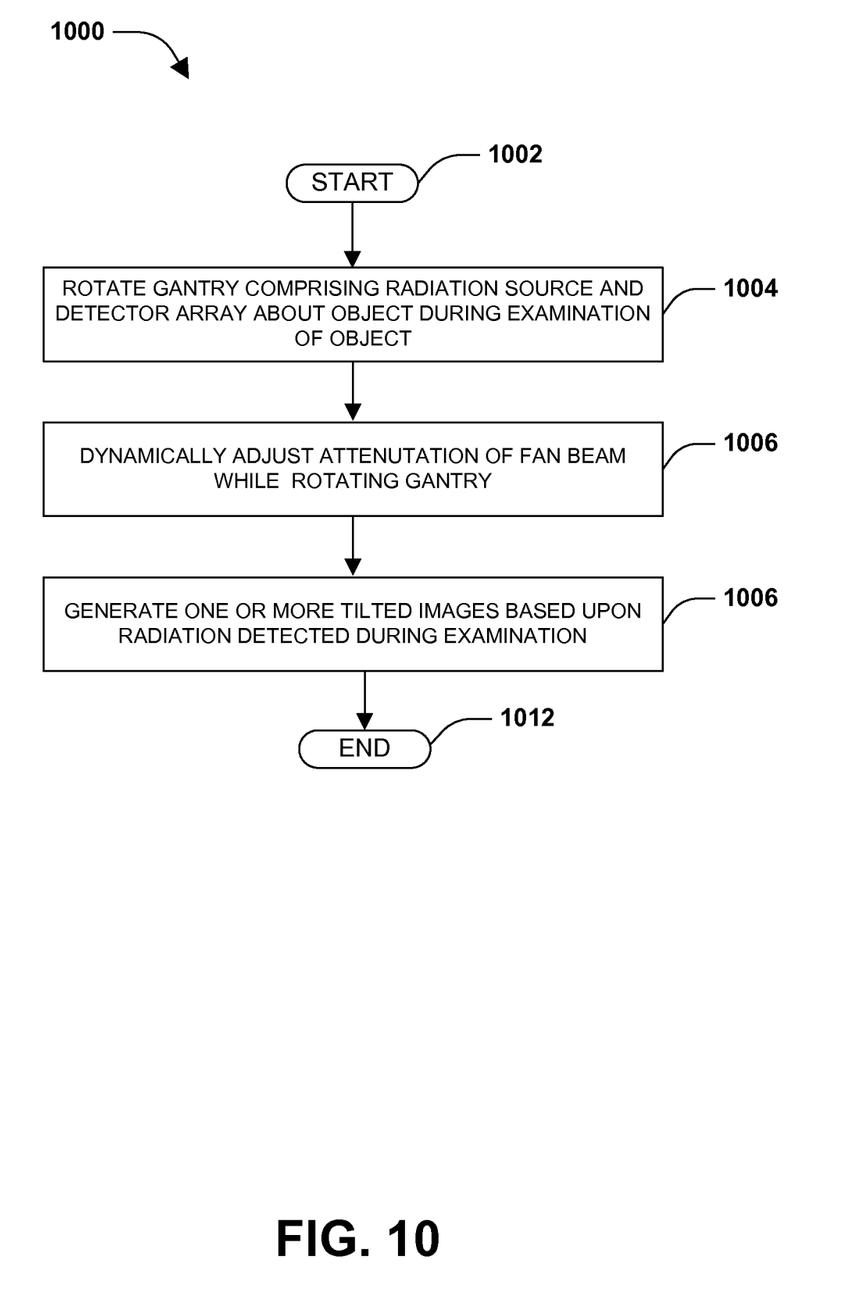
FIG. 10 is a flow diagram illustrating an example method for generating one or more tilted images.

FIG. 10 illustrates an example method 1000 which may be used in radiation imaging, for example, to digitally generate one or more tilted image slices and/or to generate one or more targeted images without tilting a field of view, for example. Such an example method 1000 may also be utilized to adjust a field of view to target portions of an object slice (e.g., such that some portions of the object slice are exposed to more radiation than other portions) (e.g., creating in effect a targeted field of view). The example method 1000 begins at 1002 and a gantry comprising a radiation source and a detector array is rotated about an object during an examination of the object at 1004. In this way, the object may be viewed from a plurality of angles to acquire volumetric data which may be utilized to reconstruct one or more images of the object, for example.

At 1006 in the example method 100, attenuation of a fan beam of radiation is dynamically adjusted while the gantry is being rotated. That is, stated differently, attenuation of radiation is adjusted in a fan-angle direction as the gantry is rotated about the object. In this way, within an object slice, portions of an object that are represented in (tilted) image(s) generated from the examination may be exposed to a greater amount of radiation than portions of the object that are not represented in the (tilted/targeted) image(s), for example.

As described above with respect to FIGS. 5-7, the radiation is attenuated prior to impinging the object under examination. For example, in one embodiment, radiation enters a pre-object collimator (e.g., such as a multi-leaf collimator) upon exiting a focal spot of the radiation source. The pre-object collimator may comprise a region of attenuation and a region of substantially no attenuation. Radiation traversing the region of substantially no attenuation may be substantially unimpeded. Radiation traversing the region of attenuation may be at least partially attenuated. For example, in one embodiment, the region of attenuation may comprise one or more radiation attenuating blades configured to attenuate at least a portion (e.g., and possibly all) of the radiation impinging the blades.

To dynamically adjust attenuation of the fan beam or to adjust attenuation, in a fan-angle direction, the region of attenuation may be dynamically resized (e.g., in the fan-angle direction) during the rotation of the rotating gantry. For example, where the region of attenuation is comprised of one or more blades, resizing the region of attenuation may comprise repositioning one or more of the blades to increase or decrease the size of the region of attenuation.

To determine a degree to which the fan beam is attenuated at a given gantry rotation angle, calculations may be performed based upon a z-position of the object support (e.g., which may be utilized to determine which slice of the object is being examined), a desired effective tilt angle of a resulting image(s), and the gantry rotation angle, for example. As such, the degree to which a fan beam is attenuated when a first object slice is being examined and/or obtained may be different than the degree to which a fan beam is attenuated when a second object slice is being examined and/or obtained, even when the gantry is at the same gantry rotation angle (e.g., as illustrated by comparing FIG. 8(*c*) to FIG. 9(*c*)), for example. Similarly, the degree to which a fan beam is attenuated for a first view of an object slice may be different than the degree to which a fan beam is attenuated for a second view of that object slice (e.g., as illustrated by comparing FIG. 8(*b*) to FIG. 8(*c*) and/or by comparing FIG. 9(*b*) to FIG. 9(*c*)), for example.

It will be appreciated that by dynamically adjusting a fan beam as the rotating gantry is rotated a portion(s) of the object under examination that is not intended to be represented in the resulting (tilted/targeted) image may be exposed to less radiation than portions of the object that are intended to be represented in the resulting image. Thus, it may be said that attenuation of the fan beam may be adjusted such that radiation that would impinge cells of the detector array that are not used during generation of the (tilted) image is at least partially attenuated.

At 1006 in the example method 1000, one or more tilted/targeted images are generated based upon radiation detected during the examination. For example, as previously described, to the extent possible, one or more non-tilted image slices of the object may be reconstructed from the information collected during the examination (e.g., interpolation techniques may be applied to the non-tilted image slices to generate one or more tilted image slices).

It will be appreciated that in one embodiment, reconstruction of one or more non-tilted images from less than a full fan-beam (e.g., which may occur if the pre-object collimator is configure to attenuate nearly 100% of the radiation traversing the region of attenuation) may introduce artifacts in the image. Therefore, in one embodiment, less than 100% of the radiation traversing the region of attenuation (e.g., 512 in FIG. 5) is attenuated. As such, the full fan-beam may be detected, with portions of the fan beam being attenuated by the pre-object collimator more-so than other portions. In such an embodiment, an image reconstructor (e.g., 124 in FIG. 1) reconstructing the non-tilted image slices, for example, may apply one or more correction techniques to approximate attenuation values for detector cells that detected radiation that was attenuated by the pre-object collimator. While the approximation may have a relatively high error rate (e.g., 10% or more), such a high error rate may be negligible because portions of the image slice(s) representing the approximated attenuation values are typically not used when interpolating to create non-tilted images (e.g., because the portions of the image slice representing the approximated attenuation values are typically representative of a portion of the object not represented in the one or more titled/targeted images), for example.

The example method 1000 ends at 1012.

Figure 11:
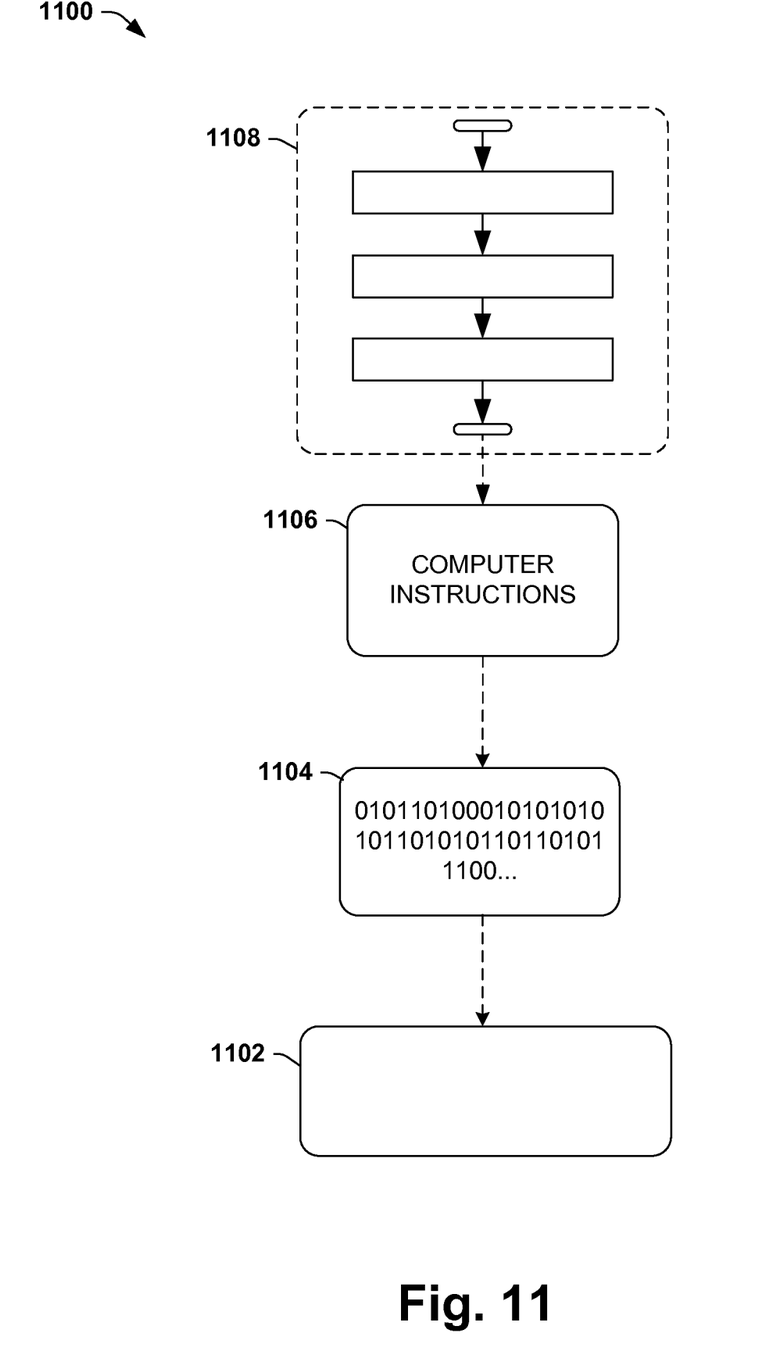
FIG. 11 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 11, wherein the implementation 1100 comprises a computer-readable medium 1102 (e.g., a CD-R, DVD-R, or a platter of a hard disk drive), on which is encoded computer-readable data 1104. This computer-readable data 1104 in turn comprises a set of computer instructions 1106 configured to operate according to one or more of the principles set forth herein. In one such embodiment 1100, the processor-executable instructions 1106 may be configured to perform a method 1108, such as the example method 1000 of FIG. 10. In another such embodiment, the processor-executable instructions 1106 may be configured to implement a system, such as at least some of the exemplary environment 100 of FIG. 1, for example. Many such computer-readable media may be devised by those of ordinary skill in the art that are configured to operate in accordance with one or more of the techniques presented herein.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B and/or the like generally means A or B or both A and B.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A computed tomography (CT) imaging modality, comprising:
   an ionizing radiation source configured to emit ionizing radiation, the ionizing radiation comprising at least one of x-ray radiation or gamma radiation;
   a detector array configured to detect at least some of the ionizing radiation; and
   a pre-object collimator configured to dynamically adjust, in a fan-angle direction, attenuation of the ionizing radiation during an examination of an object as a function of an effective digital tilt of the CT imaging modality, the effective digital tilt corresponding to a specified tilt angle of a tilted image slice relative to a rotational plane of at least one of the ionizing radiation source or the detector array.

2. The CT imaging modality of claim 1, the pre-object collimator comprising a region of substantially no attenuation and a region of attenuation.

3. The CT imaging modality of claim 2, the pre-object collimator configured to dynamically adjust attenuation of the ionizing radiation by dynamically adjusting a size of the region of substantially no attenuation.

4. The CT imaging modality of claim 3, the region of attenuation comprising one or more blades.

5. The CT imaging modality of claim 4, a blade of the one or more blades configured to be dynamically repositioned during a rotation of at least one of the ionizing radiation source and the detector array to dynamically adjust the attenuation of the ionizing radiation.

6. The CT imaging modality of claim 2, the region of attenuation configured to attenuate less than all of the ionizing radiation traversing the region of attenuation.

7. The CT imaging modality of claim 1, the pre-object collimator comprising one or more blades configured to adjust attenuation of the ionizing radiation in the fan-angle direction.

8. The CT imaging modality of claim 7, a blade of the one or more blades comprising a material configured to attenuate less than one-hundred percent of the ionizing radiation impinging upon the blade.

9. The CT imaging modality of claim 7, comprising a collimator adjustment component configured to cause a blade of the one or more blades to be dynamically repositioned during rotation of at least one of the ionizing radiation source or the detector array as a function of a trajectory of the ionizing radiation relative to the object.

10. The CT imaging modality of claim 1, comprising an image reconstructor configured to generate the tilted image slice, and the pre-object collimator configured to dynamically adjust attenuation of the ionizing radiation in the fan-angle direction as a function of detector cells utilized to generate the tilted image slice.

11. The CT imaging modality of claim 1, the CT imaging modality not configured to mechanically tilt.

12. A method for imaging an object, comprising:
dynamically adjusting attenuation of an ionizing fan beam via a pre-object collimator during an examination of an object from which a tilted image slice of the object is generated as a function of an effective digital tilt corresponding to a specified tilt angle of the tilted image slice, the ionizing fan beam comprising at least one of an x-ray fan beam or a gamma-ray fan beam.

13. The method of claim 12, comprising rotating at least one of an ionizing radiation source or a detector array about the object during the examination, and the dynamically adjusting attenuation of an ionizing fan beam comprising dynamically adjusting attenuation of the ionizing fan beam while rotating the at least one of the ionizing radiation source or the detector array.

14. The method of claim 12, the dynamically adjusting attenuation of an ionizing fan beam comprising dynamically adjusting attenuation of the ionizing fan beam as a function of a position of an ionizing radiation source relative to the object.

15. The method of claim 12, comprising identifying one or more cells of a detector array from which generated information is not used to reconstruct the tilted image slice, and the dynamically adjusting attenuation of an ionizing fan beam comprising adjusting attenuation of the ionizing fan beam such that ionizing radiation of the ionizing fan beam that would impinge the one or more cells is attenuated by the pre-object collimator.

16. The method of claim 12, the dynamically adjusting attenuation of an ionizing fan beam comprising dynamically adjusting attenuation of the ionizing fan beam as a function of a z-position of the object.

17. The method of claim 12, the dynamically adjusting attenuation of an ionizing fan beam comprising:
dynamically adjusting a fan-angle direction of a region of substantially no attenuation in a pre-object collimator; and
dynamically adjusting a fan-angle direction of a region of attenuation in the pre-object collimator.

18. The method of claim 17, at least a portion of the ionizing fan beam traversing the region of attenuation being detected by a detector array.

19. A non-transitory computer readable medium comprising computer executable instructions that when executed perform a method, the method comprising:
rotating a gantry comprising an ionizing radiation source and a detector array about an object during an examination of the object, the ionizing radiation source comprising at least one of an x-ray source or gamma source; and
dynamically adjusting via a pre-object collimator, in a fan-angle direction, attenuation of ionizing radiation emitted by the ionizing radiation source while rotating the gantry to vary an amount of the ionizing radiation to which the object is exposed, the dynamically adjusting a function of an effective digital tilt corresponding to a specified tilt angle of a tilted image slice relative to a rotational plane of the gantry.

20. The non-transitory computer readable medium of claim 19, the dynamically adjusting attenuation of the ionizing radiation comprising dynamically adjusting attenuation of the ionizing radiation as a function of a position of the ionizing radiation source relative to the object.

* * * * *